(12) United States Patent
Florent et al.

(10) Patent No.: US 7,620,221 B2
(45) Date of Patent: Nov. 17, 2009

(54) SYSTEM AND METHOD FOR ENHANCING AN OBJECT OF INTEREST IN NOISY MEDICAL IMAGES

(75) Inventors: Raoul Florent, Ville d'Avray (FR); Lucile Nosjean, Rueil Malmaison (FR); Pierre Lelong, Nogent sur Marne (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 835 days.

(21) Appl. No.: 10/543,577

(22) PCT Filed: Jan. 23, 2004

(86) PCT No.: PCT/IB2004/000175
§ 371 (c)(1),
(2), (4) Date: Jul. 27, 2005

(87) PCT Pub. No.: WO2004/066842
PCT Pub. Date: Aug. 12, 2004

(65) Prior Publication Data
US 2006/0133567 A1    Jun. 22, 2006

(30) Foreign Application Priority Data
Jan. 29, 2003    (EP) ................... 03290250

(51) Int. Cl.
*G06K 9/00*    (2006.01)
(52) U.S. Cl. ..................... 382/128; 382/103
(58) Field of Classification Search .............. 382/103, 382/128, 130, 131, 132
See application file for complete search history.

(56) References Cited

U.S. PATENT DOCUMENTS

| | | | |
|---|---|---|---|
| 5,369,678 A | 11/1994 | Chiu et al. | |
| 6,088,488 A | 7/2000 | Hardy et al. | |
| 6,154,519 A | 11/2000 | Florent et al. | |
| 6,190,302 B1 | 2/2001 | Mosseri et al. | |
| 6,236,705 B1 | 5/2001 | Stergiopoulos | |
| 6,363,163 B1 * | 3/2002 | Xu et al. ................. | 382/130 |
| 6,532,380 B1 * | 3/2003 | Close et al. ............ | 600/431 |
| 2004/0022425 A1 * | 2/2004 | Avinash et al. ........ | 382/131 |

FOREIGN PATENT DOCUMENTS

DE    42 10 124 C1    9/1993

* cited by examiner

*Primary Examiner*—John B Strege

(57) ABSTRACT

The invention relates to a system and a method for detecting an object of interest in a sequence of medical images. Said viewing system comprises alarm detection means (20) for detecting a set of alarms of said object of interest in a medical image (I') at time t, in which an alarms is a set of data describing a possible location of the object. It further comprise temporal tracking means (30) for iteratively creating a set of tracks (T') at time t by associating alarms of said set of alarms (A') with tracks (T'1) at time t−1 and for choosing a track from among said set of tracks at time t in accordance with a merit criterion. Said track at time t is ended by an alarm which corresponds to a detection of said object of interest in said medical image at time t. Said viewing system advantageously accumulates temporal proofs for confirming or infirming spatial detections of alarms at time t. Detection of the object of interest is therefore made more robust to errors.

14 Claims, 10 Drawing Sheets

SYSTEM AND METHOD FOR ENHANCING AN OBJECT OF INTEREST IN NOISY MEDICAL IMAGES

FIELD OF THE INVENTION

The invention relates to a real time medical viewing system for detecting an object of interest in a sequence of medical images. The invention also relates to an image processing method to be used in said system. The invention further relates to a medical examination apparatus coupled to such a system.

The invention finds its application for example in the detection of catheters or stents in a sequence of angiographic images.

DOMAIN OF THE INVENTION

Interventional radiology procedures are widely used for the detection and treatment of many diseases and injuries. Catheter-based medical procedures are commonplace and include such medical treatments as balloon angioplasty, stent placement, and laser ablation. In such medical procedures the progress of the catheter or of any object of interest is typically monitored, within a patient's body, by an X-ray fluoroscopic imaging system.

A method for detecting an object of interest like a catheter in angiographic images during a fluoroscopic procedure is known from U.S. Pat. No. 5,369,678. Said method, which may be used in conjunction with an apparatus that confines full X-ray dosage to a central area, aims at compensating for a reduced X-ray dosage in peripheral areas of the image by an imaging enhancement. Said imaging enhancement concerns an object of interest having the following characteristics:
  relatively thin,
  begins in periphery of an image,
  has smooth edges,
  does not bend much,
  is X-ray dense as compared with its surroundings.
Said method comprises the following steps of:
  morphologically processing the image to enhance an image of said catheter,
  thresholding said enhanced image to get a binary image containing silhouettes including a silhouette of said catheter,
  analyzing regions in said binary image to find said image of said catheter by using the above-mentioned properties of said catheter,
  finding the end of said catheter.
A drawback of said method is that it generates some false alarms and some detection failures and is consequently not very robust to errors. This is due to the fact that angiographic images are noisy images and the objects of interest have a low contrast.

SUMMARY OF THE INVENTION

An object of the invention is to propose a more robust solution to detect an object of interest in a real time sequence of medical images.

A real time X-ray medical viewing system according to the invention and as described in the opening paragraph comprises:
  alarm detection means for detecting a set of alarms of said object of interest in a medical image at time t,
  temporal tracking means comprising:
    track creation sub-means for iteratively creating a set of tracks at time t by associating alarms of said set of alarms with tracks at time t−1, a track at time t−1 comprising a predicted alarm at time t and an association of an alarm at time t with said predicted alarm at time t forming a track at time t,
    decision sub-means for choosing a track from among said set of tracks at time t in accordance with a merit criterion, the alarm of said track at time t corresponding to a detection of said object of interest in said medical image at time t.

An alarm is a set of data describing a possible location of an object of interest in a medical image. Said alarm is found on the basis of a priori knowledge criteria about the appearance of a 2D projection of the object of interest in said medical image. Said criteria are usually related to contrast and shape. They allow defining appropriate spatial filtering means for extracting alarms of the object of interest. Said object of interest may have, for example, a higher contrast than the surroundings. A catheter, for example, is relatively thin, has two parallel borders, and does not bend too much. A balloon marker is a small circular or square-shaped blob.

Said alarm detection means achieve a strictly spatial detection of alarms in a medical image, i.e. the output of said alarm detection means for an image at time t is independent of the output of said alarm detection means at time t−1. However, unlike in the prior art, no decision about the best alarm is taken by the alarm detection means. On the contrary, decision is advantageously postponed to the temporal tracking means. Therefore, a number of alarms are output by the alarm detection means to the temporal tracking means. This is a method of compensating for the fact that, in the medical domain, objects of interest usually present a rather low contrast against a noisy background and that they cannot be detected with certainty most of the time, which induces both false alarms and detection failures.

A track is a set of data describing successive locations of said object of interest in a medical sequence. Said track is updated recursively by the temporal tracking means. Said temporal tracking means are able to iteratively create a set of tracks at time t by associating alarms detected in a medical image at time t with previous tracks ending at time t−1. A track ending at time t is therefore composed of alarms belonging to successive images of a sequence from time zero to time t. To be added to a track, an alarm at time t must contribute to the track regularity, for example in terms of contrast, continuity or orientation. Said temporal tracking means are further able to decide, for an image at time t, which track at time t is the most meritorious one in accordance with one or several criteria. The alarm ending said most meritorious track thus corresponds to a detection of the object of interest at time t.

An advantage of said temporal tracking means is that they accumulate temporal proofs in favor of an alarm found at time t. Best alarm selection is done by using spatial and temporal criteria and therefore becomes more robust to errors.

In a preferred embodiment of the invention, said temporal tracking means proceed in an "alarm-centric" way, i.e. said track creation means associate with an alarm at time t that track at time t−1 that minimizes a matching error. In other words, said track creation means start from an alarm at time t and search for the best track ending at time t−1 to be matched with said alarm. This search is thus made in the opposite direction compared with the track formation. Possible associations between said alarm and tracks a time t−1 are evaluated by calculation of matching errors. Only the association that minimizes the matching error for said alarm is able to compete with other associations coming from other alarms to be considered as the best track at time t according to merit criteria. A consequence is to favor the alarms detected at time t to the detriment of the tracks ending at time t−1. In this way, all the alarms are certain to be associated with a track ending at time t−1, whereas some tracks ending at time t−1 may remain unassociated. This is another way of reducing the number of detection failures.

BRIEF DESCRIPTION OF THE DRAWINGS

The invention will be further described with reference to the accompanying drawings.

DETAILED DESCRIPTION OF THE INVENTION

The invention relates to a viewing system and to a method that is used to actuate the viewing system for detecting an object of interest in real time in a sequence of medical images. The viewing system and the method of the invention are described hereinafter as a example in an application to the medical field of cardiology. In said application, the object of interest is an organ such as an artery or a tool such as a balloon or a stent. These objects are observed during a medical intervention called angioplasty or Percutaneous Transluminal Coronary Angioplasty (PTCA), in a sequence of X-ray fluoroscopic images called angiogram.

It is to be noted that the system and method may be applied to any object of interest other than a stent, an artery or a catheter in images other than angiograms, for example to the tracking of a biopsy needle in a sequence of breast ultrasound images. In the following, the invention is described in the particular case of a single object of interest, but it may also be applied to several objects of interest, like several stents.

Figure 1A:
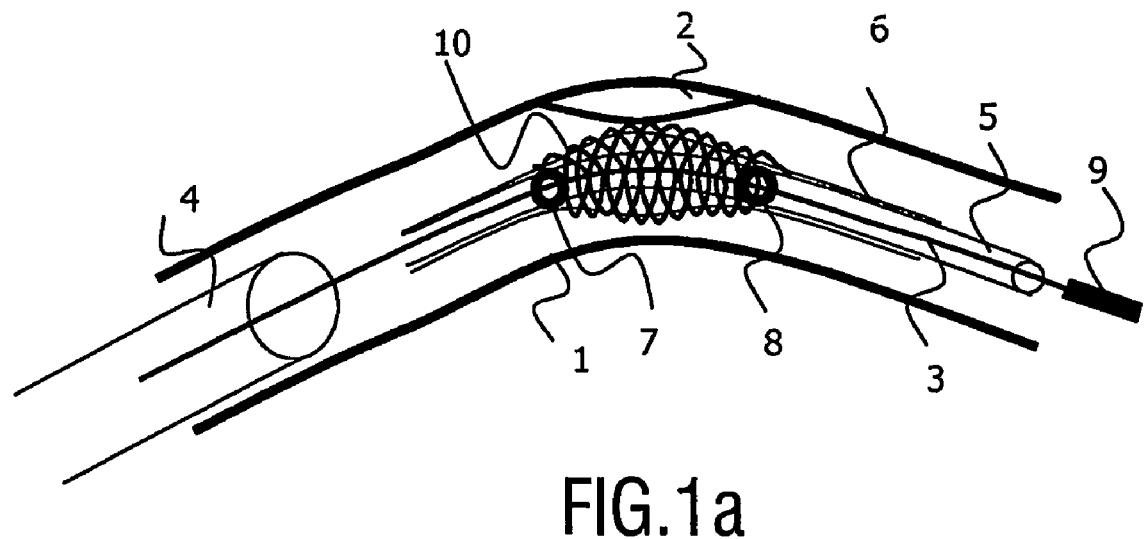
FIGS. 1a and 1b illustrate a procedure of stent deployment at a stenosis location.
Figure 1B:
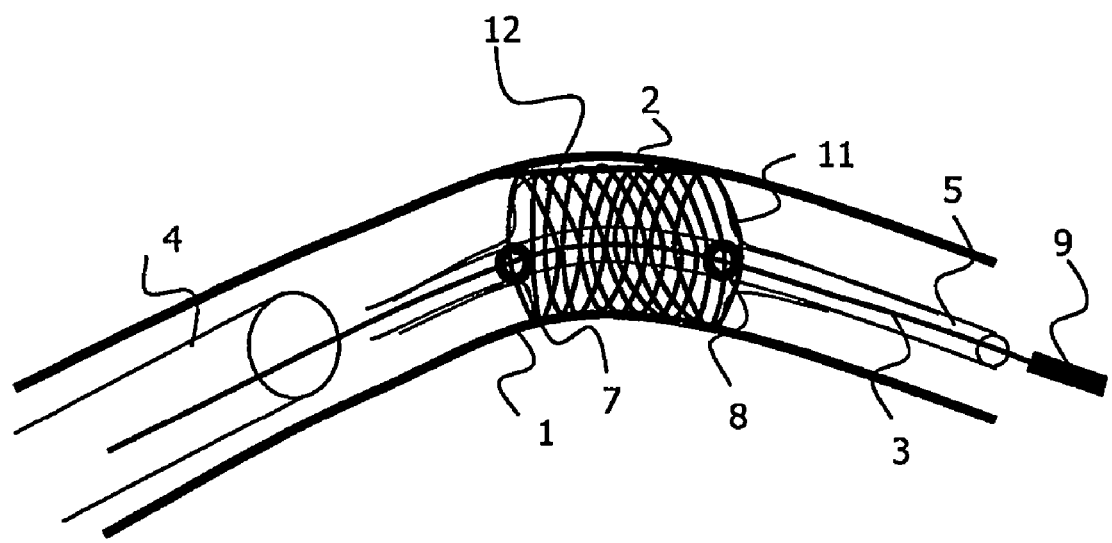

Referring to FIGS. 1a and 1b, in the application described hereinafter, the stent implantation is a medical intervention, which consists in enlarging an artery at the location of a lesion called stenosis. Firstly, the practitioner localizes a stenosis 2 on a patient's artery 1 in the sequence of images. Then, he introduces a thin guide wire 3 through the lumen of the artery 1 using a catheter 4. Said guide-wire 3 is passed to beyond the stenosis 2. It is to be noted that said guide wire 3 has a radio-opaque tip 9 at its extremity, which helps the practitioner to check on a sequence of images whether the guide-wire 3 has been correctly introduced. A thin tube 5 denoted a monorail is then easily slipped over the guide-wire 3 and placed in the stenosis area. Said monorail 5 has a balloon 6 wrapped around it and a stent 10 put over said balloon 6. Said balloon 6 has two radio-opaque balloon markers 7 and 8 that help the practitioner place the balloon 6 in the right position with respect to the stenosis 2. The balloon 6 is inflated to become an inflated balloon 11 and to expand the stent 10, which thus becomes an expanded stent 12. Then, the inflated balloon 11, the monorail 5, the guide-wire 3 and the catheter 4 are removed, so that the expanded stent 12 serves as a permanent implant.

A key point of the intervention is to place the stent properly in the stenosis area. To this end, the practitioner visualizes the area of the stenosis in real time on a sequence of images several times during the intervention.

In a preferred embodiment of the invention, the object of interest is a stent or a stenosis. The problem is that such an object of interest is a weakly radio-opaque object of interest, which is moving against a moving background. Therefore, the stent or the stenosis is preferably detected indirectly by location of related balloon markers. Said balloon markers are disposed at each extremity of the balloon. The balloon markers are particularly recognizable because they constitute punctual zones, practically black or at least dark in the angiographic images. They are also very similar in shape. It should be noted that the tip 9 of the guide wire 3 may also be used as a marker for indirectly detecting the stent 12.

Figure 2:
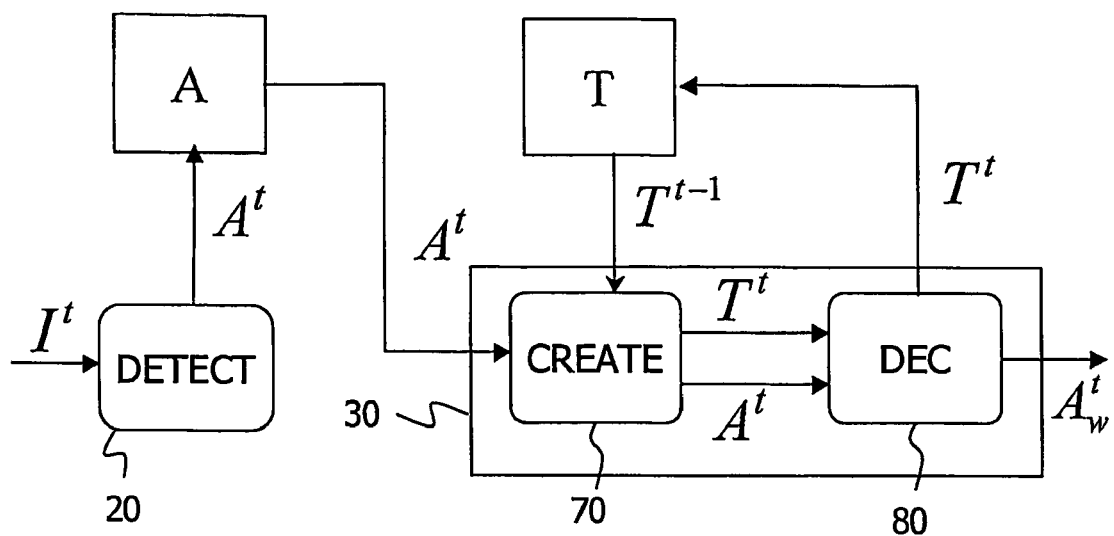
FIG. 2 is a functional block diagram of the detection and the temporal tracking means according to the invention.
Figure 3:
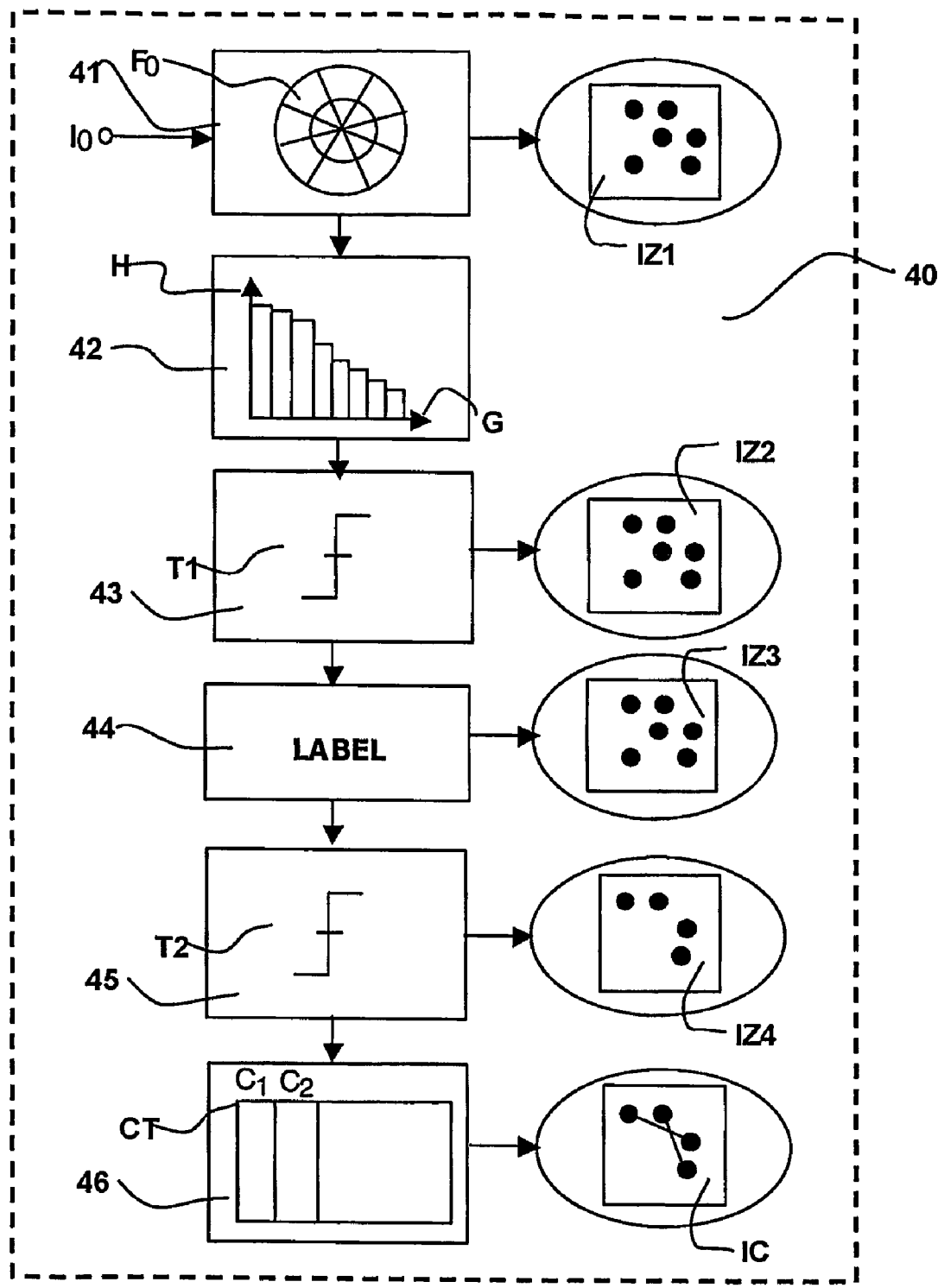
FIG. 3 is a functional block diagram of the marker detection sub-means according to the preferred embodiment of the invention.
Figure 4A:
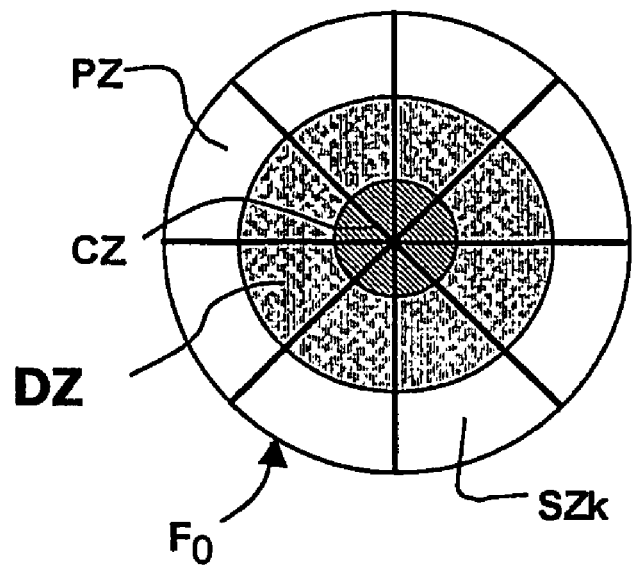
FIG. 4a shows a circular filter for extracting balloon markers according to the invention.

As shown in FIG. 2, the viewing system according to the invention comprises alarm detection means 20 for detecting a set of alarms of said object of interest in a sequence of images. The alarm detection means 20 comprise marker extraction sub-means 40, which perform elementary measures for extracting candidates of markers and forming candidates of couples of markers, as shown in FIG. 3. Said marker extraction sub-means 40 comprise several elementary measure sub-means, which are intended to characterize the candidates of markers:

First measure means 41 that select punctual dark zones contrasting against a brighter background: This measure is provided by filter means denoted $F_0$. In a preferred example, referring to FIG. 4a, an appropriate filter comprises three circular concentric zones, including a central zone CZ, a dead zone DZ, and a peripheral zone PZ. The filter $F_0$ is further divided into n sectoral zones SZ covering 360° and numbered 1 to n. A current sectoral zone $SZ_k$ is numbered k with $1 \leq k \leq n$. The first measure consists in scanning a current image of the sequence of images in order to look for a punctual dark zone. A punctual dark zone can be detected if said punctual dark zone is centered in the filter. When a punctual dark zone is centered, it occupies the central zone CZ of the filter, and it possibly occupies a part of the dead zone DZ. The first measure is based on the estimation of contrast of intensity between the central zone CZ and the peripheral zone PZ. Said estimation of contrast may be carried out by estimating the difference in average intensities between the central zone CZ and peripheral zone PZ. This simple measure would lead to a linear estimation of the contrast. In order to refine the result of this estimation, the first measure is actually carried out by calculating the minimum of the n average intensities determined in the n peripheral sectoral zones separately. These minimum intensities are denoted:

$I_{Pk}$ = average intensity in the peripheral sectoral zone numbered $k$, and $I_{CZ}$ = average intensity in the central zone $CZ$.

The final measure provided by the filter $F_0$ is: $I_{F0} = \min_k(I_{Pk}) - I_{CZ}$ This measure $I_{F0}$ is determined by scanning each pixel of the original image $I_0$ with the filter $F_0$. It provides an enhanced images denoted IZ1, of Punctual dark zones, denoted Z, where all other structures have disappeared, with the exception of said punctual dark zones that are now candidates to constitute markers.

Second measure means 42 comprising histogram means denoted H: In this image IZ1, each pixel has a gray level. From the image IZ1, a histogram is constructed which represents the different numbers H of pixels corresponding to each gray level value G. Toward the right of the axis G in FIG. 3 are the high gray level values; and toward the left of axis G are the low gray level values. For each gray level value G, the height H of the box represents the number of pixels to be found having said gray level value. Since the average size of a punctual dark zone Z is determined by the characteristics of the filter $F_0$, it is possible to estimate the size of a punctual zone in pixels. Assuming that the size of a punctual zone is p pixels, and assuming that, for example, a number z of zones is to be found in the image IZ1, a search is made for a number of p.z (p times z) pixels that have the highest gray levels. The histogram H, as shown in FIG. 3, permits of accumulating the number of pixels in adjacent boxes, starting from the right of axis G, until the estimated number of p.z pixels is reached for the image, i.e. for z zones of p pixels each, while choosing the p.z pixels having the highest gray levels i.e. the pixels in the boxes on the right of the G axis. The histogram H permits of determining a gray level $G_H$ which yields the p.z pixels.

Third measure means 43 comprising threshold means denoted $T_1$: A first intensity threshold $T_1$ is then applied to the image IZ1. The threshold $T_1$ is chosen to be equal to the previously determined gray level $G_H$. That permits of selecting in the image IZ1 said number p.z of pixels having at least a gray level equal to $G_H$. A new image is formed in which the intensities and the coordinates of the pixels are known, thus forming the image of points IZ2.

Fourth measure means 44, called label means, which perform a connexity analysis on pixels previously selected for the image IZ2, in order to connect pixels pertaining to a same punctual dark zone Z. The labeling means 44 provide a number of labeled punctual dark zones in a new image IZ3.

Fifth measure means 45 comprising second threshold means $T_2$: This second threshold $T_2$ is applied, for example, to the intensities of the pixels of the image IZ3 of labeled zones and to the diameter of the zones in order to select the best labeled zones. For example, $T_2$ equals a product of a given intensity by a given diameter, for selecting a number of remaining punctual zones having the highest intensities and the best shapes for constituting markers, thus yielding an image of markers IZ4.

Sixth measure means 46 using a table, denoted CT: This table CT of possible couples $C_k$ (k integer) of selected punctual dark zones is constructed on the basis of the a-priori known distance IM between the markers, with an incertitude of, for example, 20%. The table CT provides an image IC of the possible marker couples $C_k$.

In the preferred embodiment of the invention, said alarm detection means 20 further comprise alarm conversion sub-means in order to convert couples of markers into alarms. A couple of markers $C_k$ are for instance described by the locations $m_{k1}$, $m_{k2}$ of said markers and a strength measure $s_k$, that is: $C_k=(m_{k,1},m_{k,2},s_k)$. Said strength measure represents the strength of the detection and is for example equal to a gradient intensity.

Figure 4B:
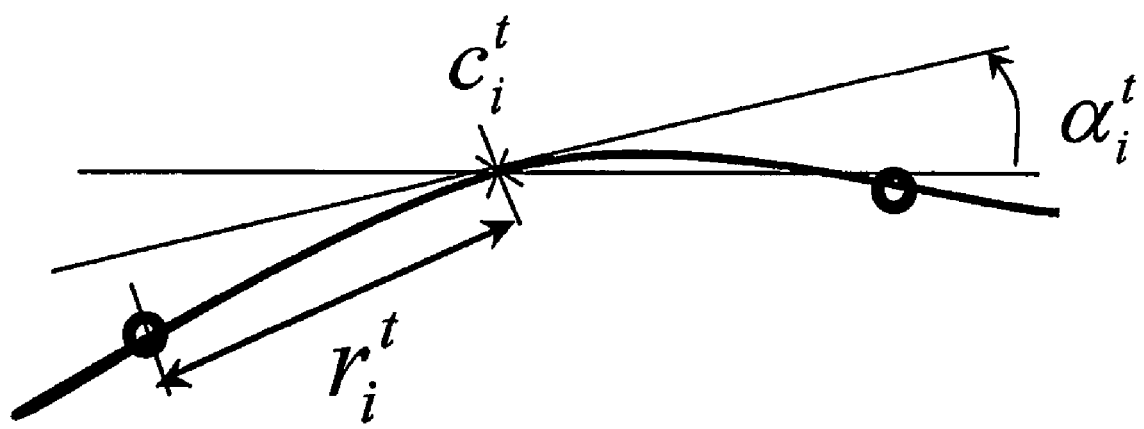
FIG. 4b depicts some shape attributes used to describe a couple of balloon markers.

Objects of interest in medical images often have a low contrast and suffer from a noisy background, but they usually have shape attributes that may help discriminate them among false detections. For example, a stent is an elongated object whose orientation evolves in the same way as the artery in which it is placed with a known and constant distance between its pair of balloon markers. Referring to FIG. 4b, an alarm $A_i^t$ (i is an integer) of a couple of markers $C_k$ is advantageously described by a vector of characteristics VC comprising a barycenter location $c_i^t$, an orientation $\alpha_i^t$, and a radius $r_i^t$. In addition, said alarm may be represented by a confidence measure, for example equal to the marker couple strength measure $s_i^t=s_k$. In the preferred embodiment of the invention, said alarm conversion sub-means thus convert a couple of markers $C_k=(m_{k,1},m_{k,2})$ and a strength measure $s_k$ of an image at time t into an alarm $A_i^t=(VC(c_i^t,\alpha_i^t,r_i^t),s_i^t)$.

Said alarm detection means 20 supply a number of alarms forming a set of alarms $A^t$ for an image $I^t$ at time t. Decision about a best or winning alarm is not made at this stage, but preferably postponed to the temporal tracking means 30. As a matter of fact the alarm detection means 20 are unable to detect the object of interest with certainty. In the preferred embodiment of the invention, a dozen of alarms are output. It is found that a dozen of alarms per object of interest are needed in order to limit the number of detection failures to an acceptable level.

As shown in FIG. 2, the viewing system according to the invention further comprises temporal tracking means 30 comprising:

track creation sub-means for iteratively creating a set of tracks ($T^t$) at time t by associating alarms of said set of alarms ($A^t$) with tracks ($T^{t-1}$) at time t−1, a track a time t−1 comprising a predicted alarm at time t and an association of an alarm at time t with said predicted alarm at time t forming a track at time t, decision sub-means for choosing a track from among said set of tracks at time t in accordance with a merit criterion, the alarm of said track at time t corresponding to a detection of said object of interest in said medical image at time t.

The aim of said temporal tracking means is to provide temporal proofs for confirming or infirming the alarms spatially detected by said alarm detection means 20.

A track $T_j^t$ at time t, where j is an integer, links alarms detected in the previous images of said medical sequence from time t=0 to time t. Said track $T_j^{t1}$ is advantageously described by a set of data which are updated recursively. Advantageously, said set of data comprises a description of the alarm ending said track at time t or a prediction of an alarm which could contribute to extending said track at time t+1 and some material for managing the lifetime of said track, such as an index of a previous track from which said track stems or a merit value. A track at time t may therefore be recursively defined as an association of an alarm $A_i^t$ and a predicted alarm $Ap_j^t$ of a track $T_j^{t-1}$ at time t−1.

In an embodiment of the invention, said track comprises a vector of characteristics which describes either the alarm ending said track at time t or a prediction of the alarm which could extend said track at time t+1. Said vector of characteristics is defined in the same vectorial space as the vector of characteristics previously defined for an alarm. In the preferred embodiment of the invention dealing with stent detection in a sequence of cardiac images, said vector of characteristics advantageously comprises a barycenter component, an orientation component, and a radius component.

Figure 5:
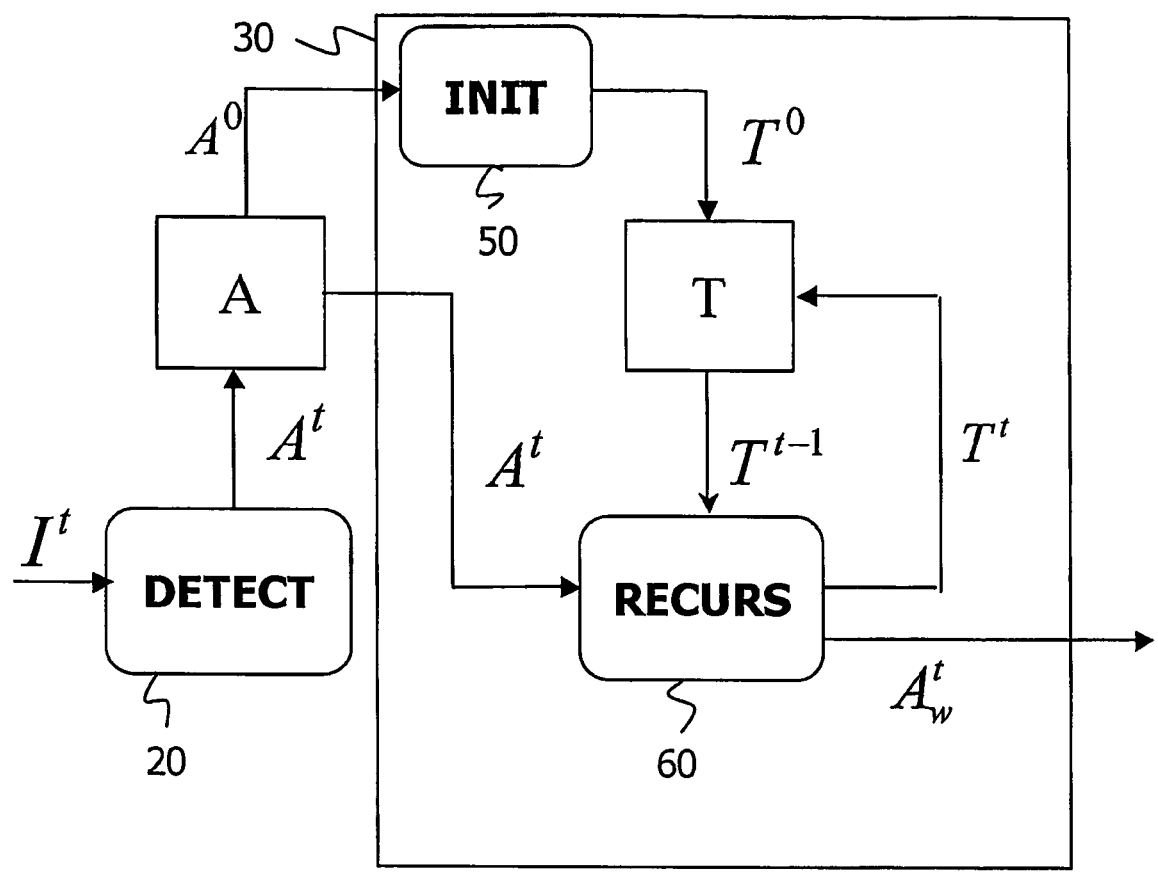
FIG. 5 depicts in a functional way the initialization and the recursive sub-means of the temporal tracking means according to the invention, FIG. 6a describes the way tracks at time t are formed from alarms at time t and tracks at time t−1.

As already mentioned, said temporal tracking means 30, which involve an iterative process, comprise initialization sub-means 50 and recursive sub-means 60, as shown in FIG. 5. Said initialization sub-means derive a first set of tracks $T^0$ at time t=0 from a set of alarms $A^0$ at time t=0. Since no history material is available at that stage, said initialization sub-means must rely solely on the set of alarms $A^0$ at time t=0. The output set of tracks $T^0$ is thus composed of tracks comprising a single alarm. A track $T_j^0$ is given a strength measure equal to the strength measure of the alarm $A_i^0$.

Said recursive sub-means 60, which start operating from time t=1, build a set of tracks at time t from a set of alarms at time t provided by the alarm detection means and a set of previous tracks at time t−1.

Figure 6A:
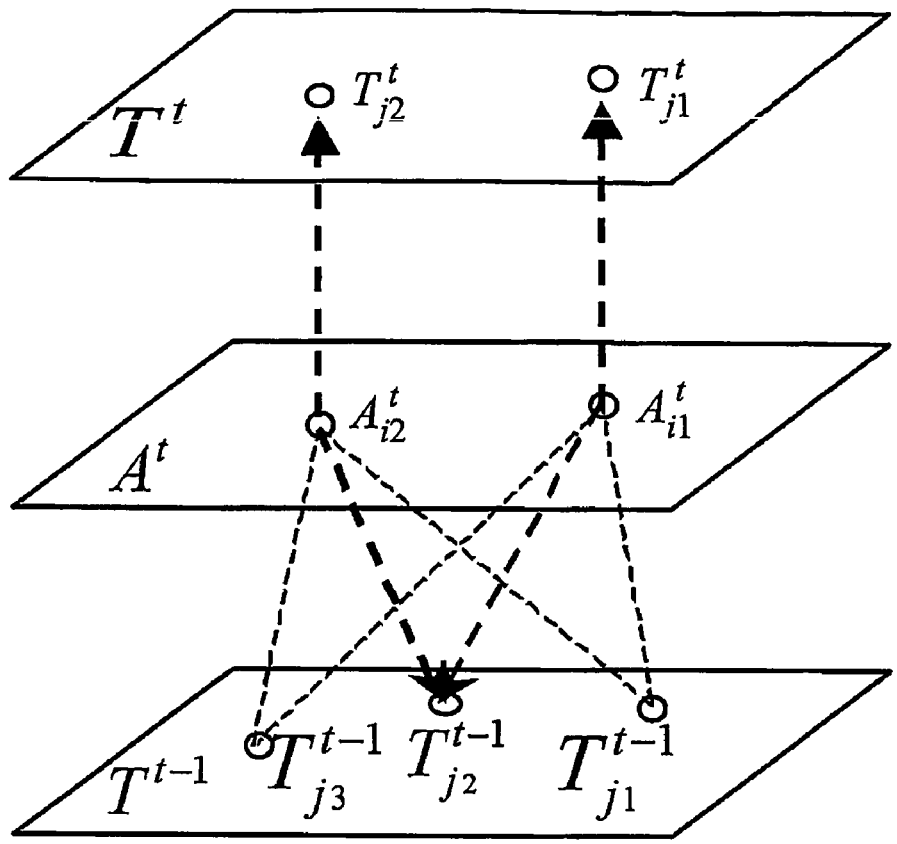
FIG. 6b shows a fuzzy function to be applied to the matching error.

Referring to FIG. 5, said recursive sub-means comprise:

Track creation sub-means 70 for creating a set of new tracks at time t, by associating alarms found in the image at time t with previous tracks ending at time t−1. In the preferred embodiment of the invention, an "alarm-centric" strategy is used. Instead of defining mechanisms for extending the tracks found at time t−1 to time t, the track creating sub-means 70 create one new track per alarm at time t and forget about the previous tracks, as shown in FIG. 6a. All the possible associations between said alarm $A_i^t$ and the previous tracks $T_j^{t-1}$ are tested using a matching error $E_{i,j}^t$. The association $(A_i^t, T_j^{t-1})$, which minimizes said matching error, forms a new track $T_j^t$. In the following, said matching error is also called a raw matching error. In an embodiment of the invention, both the alarm at time t and the predicted alarm at time t−1 of the track at time t−1 are described by a similar vector of characteristics. In this case, said matching error $E_{i,j}^t$ is a composite error, which is calculated for each component of said vector of characteristics. In the preferred embodiment of the invention, said composite error therefore comprises a barycenter part corresponding to a normalized distance between barycenters, an orientation part corresponding to normalized angle differences, and a radius part corresponding to a radius variation. An advantage of such a composite error is that it characterizes more precisely the matching error caused by the association of said alarm with said previous track than does a global error, and consequently that it discriminates more efficiently between false alarms and true detections. For example, it may be assumed that the orientation of an artery or a stent changes regularly from an image to another. Consequently, a high orientation error calculated for an association of an alarm with a previous track may mean that said association is not valid, even if the barycenter and radius errors are low. A global error with a mean value may have missed such a variation in orientation and consequently have led to the opposite result. In other words, a composite error allows the definition of different ranges of variations for the different components of said error.

Figure 6B:
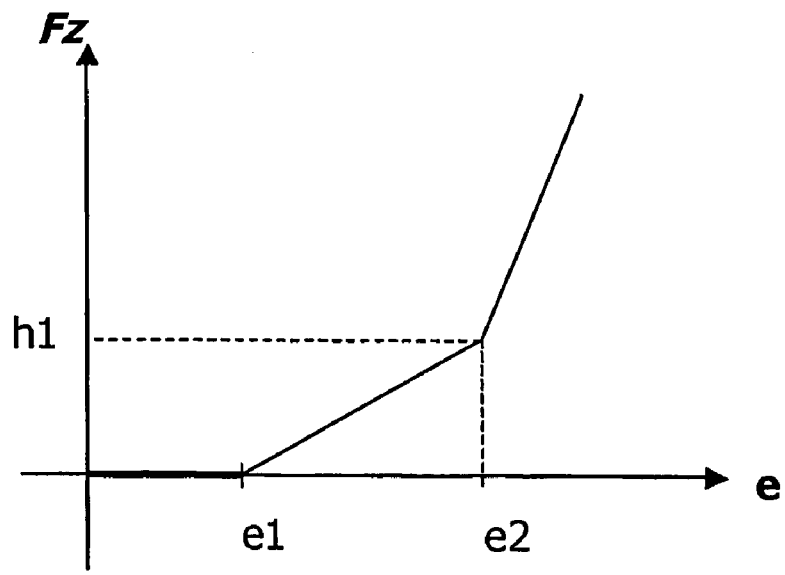

In the medical domain objects of interest are sensitive to noise because of their low contrast. They are also likely to have imprecise and unpredictable displacements, which are due, for example, to cardiac pulses and respiratory movements and also to the fact that said objects of interest are two-dimensional projections of a three-dimensional world. Such imprecise and unpredictable displacements make a strict evaluation of matching errors difficult. However, the fact that the amplitude of said movements is well known renders it possible to delimit some variation ranges, in which an error value is considered as negligible, or in the opposite case in which said error value is considered as clearly indicating a mismatch between an alarm and the predicted alarm of a track. Consequently, in the preferred embodiment of the invention, said raw matching error $E_{i,j}^t$ is converted into a fuzzy matching error $E_{Fzi,j}^t$. Said fuzzy matching error is obtained by applying to said raw matching error a non-linear weighting function Fz, that is: $E_{Fzi,j}^t = Fz(E_{i,j}^t)$ Said non-linear weighting function Fz strongly penalizes high errors while equalizing the impact of comparatively weak errors. An example of such a fuzzy weighting function is given in FIG. 6b. Said fuzzy weighting function defines, for example, three zones. A first one $[0, e_1[$ may correspond to equivalently weak errors considered as negligible. The second one $[e_1, e_2[$ may correspond to nominal errors which are treated linearly. The last one $[e_2, \infty[$ corresponds to out-of-range errors, which are therefore penalized with a strong increase of the slope of a final linear segment. An advantage of such a fuzzy matching error is that the method is made more robust to small spatial detection errors.

The track creation sub-means 70 finally output a single new track per alarm at time t.

Decision sub-means 80 for choosing a track from among said set of tracks at time t in accordance with a merit criteria, the alarm of said track at time t corresponding to a detection of said object of interest in said medical image at time t. In the preferred embodiment of the invention, said merit criteria of a track at time t are calculated as a combination of the temporally integrated alarm strength and the temporally integrated matching error. Temporal integration consists in applying a first-order recursive filter to the alarm strength and the matching error. It should be noted that said matching error may be raw or fuzzy. Said recursive filter averages out the past and present contributions to said alarm strength and said matching error respectively. Such a first-order recursive filter y can be expressed as follows: $y(t)=y(t-1)+\beta.(x(t)-y(t-1))$, where x is a function of time, $\beta$ a real weighting factor, and y(t) the temporally integrated version of x(t) at time t. (x(t)−y(t−1)) stands for a correcting term. A temporally integrated version $\bar{E}_j^t$ of the matching error $E_{i,j}^t$ can be derived from the expression of y(t): $\bar{E}_{i,j}^t = \beta.\bar{E}_{i,j}^t + (1-\beta).\bar{E}_j^{t-1}$ Said merit criterion is, for example, a linear combination of said integrated alarm strength and said integrated matching error: $M_{i,j}^t = (1-\theta).\bar{E}_{i,j}^t + \theta.\bar{S}_i^t$, $\theta$ is a real value which belongs to $]0, 1[$.

In the preferred embodiment of the invention, said track at time t comprises, in addition to the vector of characteristics of an alarm at time t or a predicted alarm which could extend said track at time t+1, the temporally integrated matching error, the temporally integrated strength, and the merit criterion $M_{i,j}^t$.

In other words, said decision sub-means consist in deciding which alarm $A_i^t$ leads to the most predictable and strongest track $T_j^t$. The winning alarm $A_w^t$ at time t is the one leading to the highest merit $M_{i,j}^t$. Said winning alarm $A_w^t$, which is output, corresponds to a detection of the object of interest. The whole set $T^t$ of tracks formed at time t will serve at the next iteration as a basis for creating new associations of alarms and tracks at time t+1.

If several objects of interest are tracked, the above-mentioned decision means will choose several tracks at time t, for example the tracks whose merit is greater than a predetermined threshold.

In the preferred embodiment of the invention, the temporal tracking means 30 according to the invention do not include any prediction model for predicting a track at time t from the knowledge of a track at time t−1. As was explained above, the displacements of objects of interest in the domain of cardiology like arteries, catheter or stents during a sequence are not easily predictable due to respiratory movements, other patient movements and cardiac pulses, and therefore an appropriate model of prediction cannot be found easily. As a consequence, the predicted alarm $Ap_i^{t+1}$ of a track a time t corresponds to the alarm $A_i^t$ ending said track at time t.

Figure 7A:
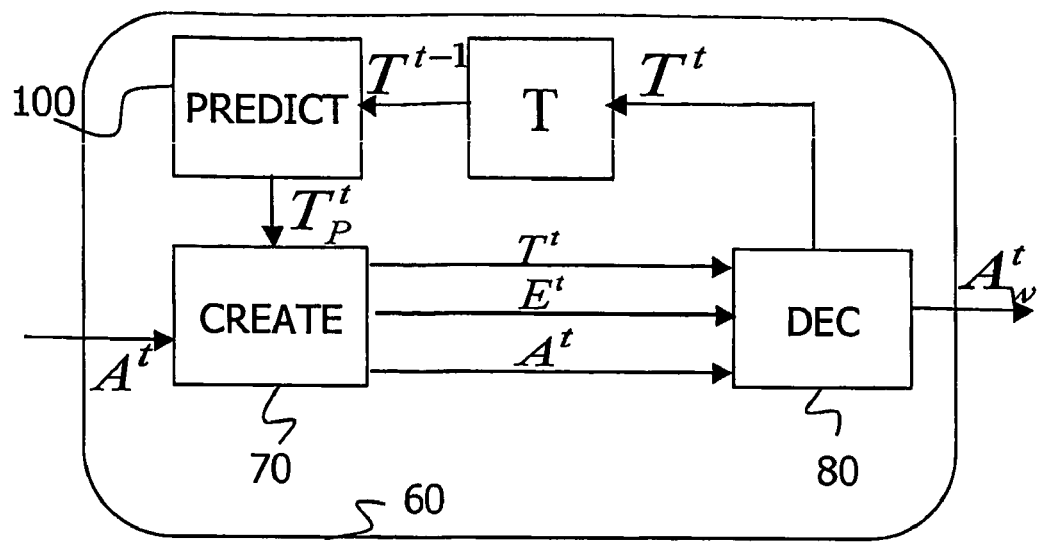
FIG. 7a is a functional block diagram of the temporal tracking means comprising prediction means for predicting a track at time t from a track at time t−1.
Figure 7B:
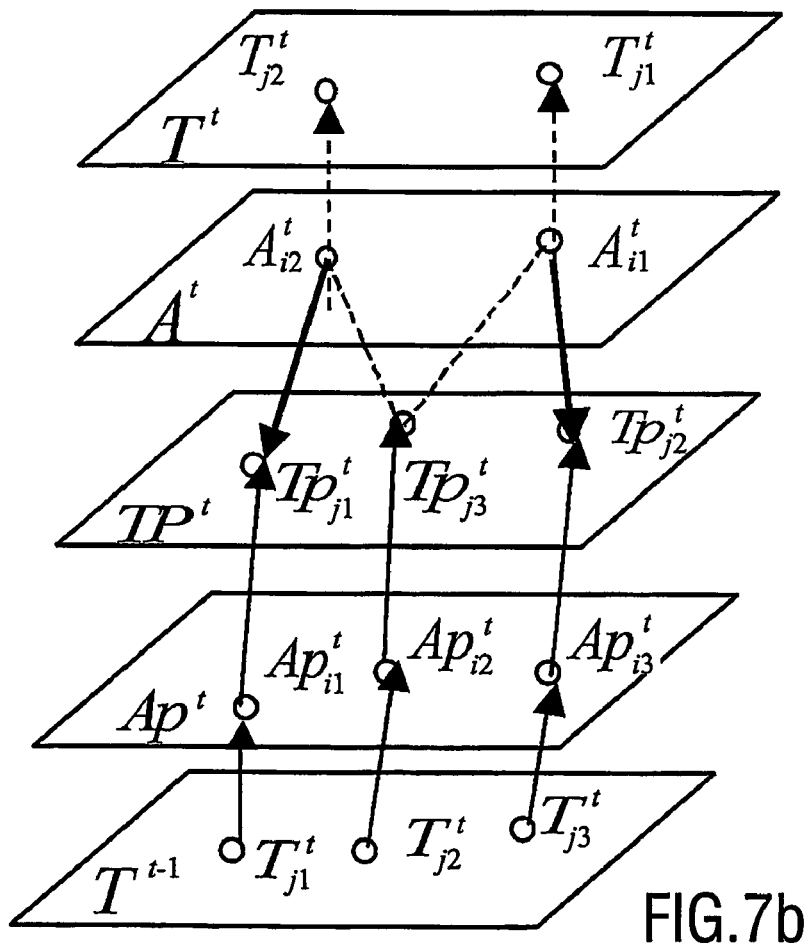
FIG. 7b shows a predicted track formed at time t from a track at time t−1.

It is to be noted that the temporal tracking means 70 work very well without any predictor. It may also be due to the fact that, as in most medical images, focus is made on the object of interest. A consequence is that said object of interest never disappears from the image. It may even be assumed that said object of interest only has limited displacements around a mean position, provided that the patient does not have other movements than respiratory movements and heart motion, However, in another embodiment of the invention, for example dealing with a sequence of carotid images where a translational table movement may be applied, a simple model of prediction can be used. Consequently, said temporal tracking means 30 comprise prediction sub-means 100 for predicting a track $Tp_j^t$ at time t from a track $T_j^{t-1}$ at time t−1, as shown in FIGS. 7a and 7b. Said predicted track $Tp_j^t$ at time t is used instead of said $T_j^{t-1}$ at time t−1. Said predicted track at time t comprises a predicted alarm at time t, which could extend said track at time t, instead of an alarm ending said track at time t−1. In this particular case, an advantageous prediction model may be, for example, a first-order predictor based on the assumption of constant alarm speed along a track. Said speed is estimated as a temporal integration of the variation of the alarm positions along said track.

It should be noted that said prediction model is only used for predicting an alarm $Ap_i^t$ at time t which could extend a track $T_j^{t-1}$ at time t, but does not affect other fields of the track such as the merit value $M_j^t$. In other words, the predicted track $Tp_j^t$ strictly corresponds to the above-mentioned track $T_j^{t-1}$ comprising a predicted alarm $Ap_i^t$ at time t.

It may happen that none of the number of alarms output at time t by the alarm detection means matches well with a track at time t−1. In other words, the best association between alarms at time t and tracks at time t−1 may lead to a merit that is below a predetermined threshold, indicating that said association is not relevant. It should be noted that such a predetermined threshold is given a value which is strongly dependent on the application.

Figure 8A:
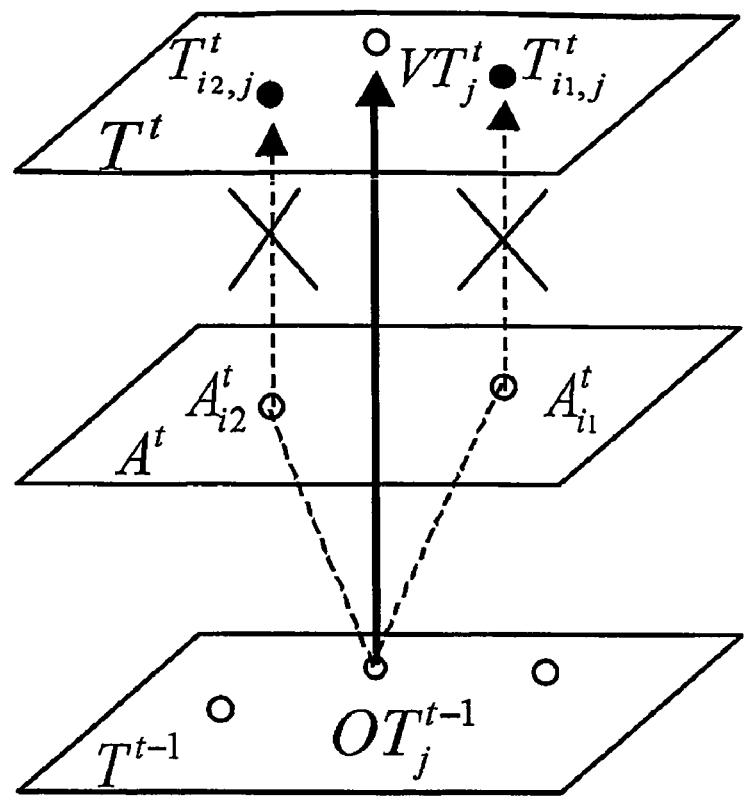
FIG. 8a is a functional block diagram of the temporal tracking means comprising virtual track creation means for a virtual track at time t from an orphan track from time t−1 or an orphan alarm at time t.
Figure 8B:
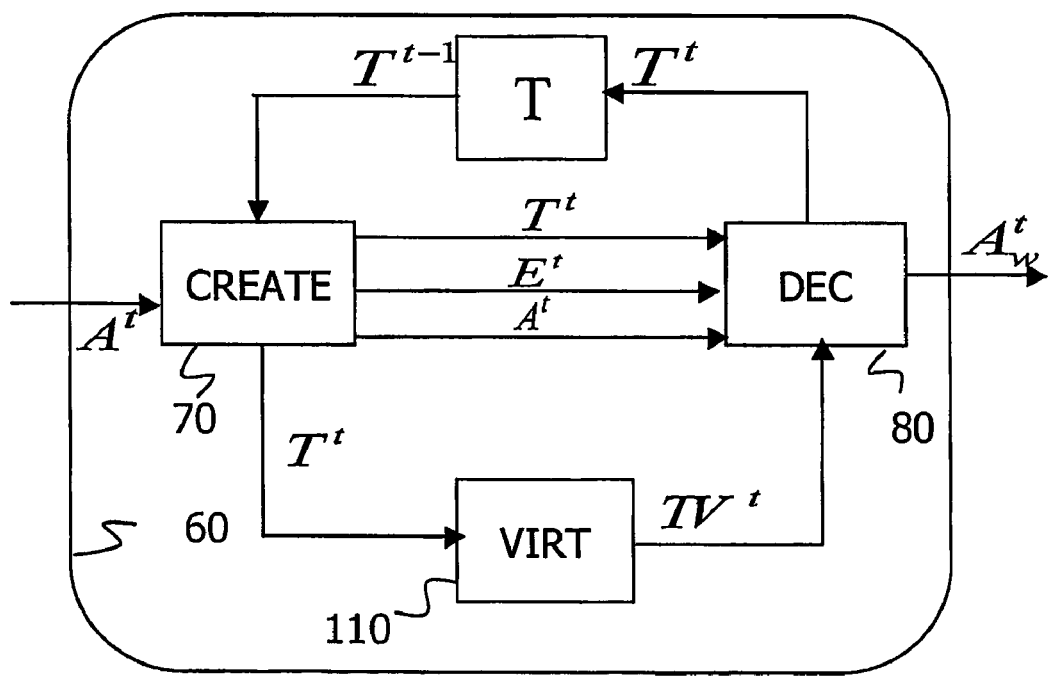
FIG. 8b shows how a virtual track is formed at time t from an orphan track at time t−1.

Such a situation may occur when the alarm detection means have had some detection failures. In the domain of cardiology, this is the case for about 20 percent of the images of an angiogram. In this situation, a reliable track at time t−1 remains unassociated or is badly associated at time t, as shown in FIG. 8a. Such a track is called an orphan track $OT_j^t$. In the preferred embodiment of the invention, the temporal tracking means 30 further comprise virtual track creation means 110 for compensating for the absence of relevant alarms. Said virtual track creation means 110 consist in:

finding the most reliable track at time t−1,
checking whether said track gave birth to one or more child tracks at time t,
if this is the case, checking whether the most reliable child track at time t has a raw matching error value below a predetermined raw error threshold,
if yes, taking as the best alarm at time t the end point of said most reliable child track at time t,
if there is no reliable child track at time t, said most reliable track at time t−1 is identified as an orphan track, and a virtual track $VT_j^t$ is created in order to support the presumably absent alarm, for example by copying at time t the end point of said most reliable track at time t−1.

It should be noted that orphan alarms may occur in the case of a "track-centric" approach, when a strong alarm at time t remains unassociated.

By virtue of the fact that, in the domain of cardiology, the object of interest only has displacements of limited amplitude, which are not easily predictable, such a virtual track at time t does not need to be penalized compared with true tracks for contributing to a next iteration.

Figure 9A:
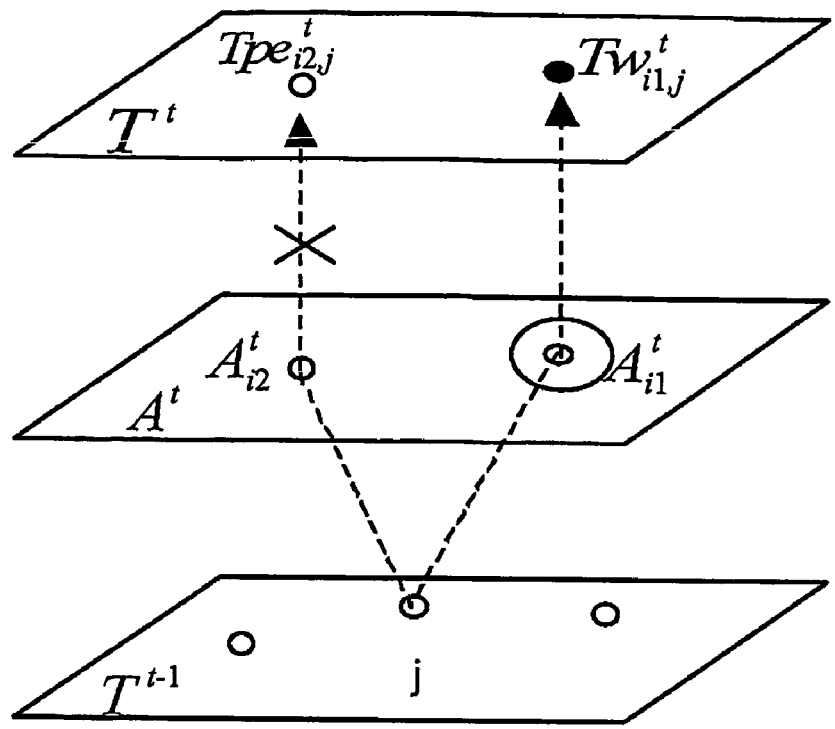
FIG. 9a shows an example of contending tracks at time t, which come from a same track at time t−1.
Figure 9B:
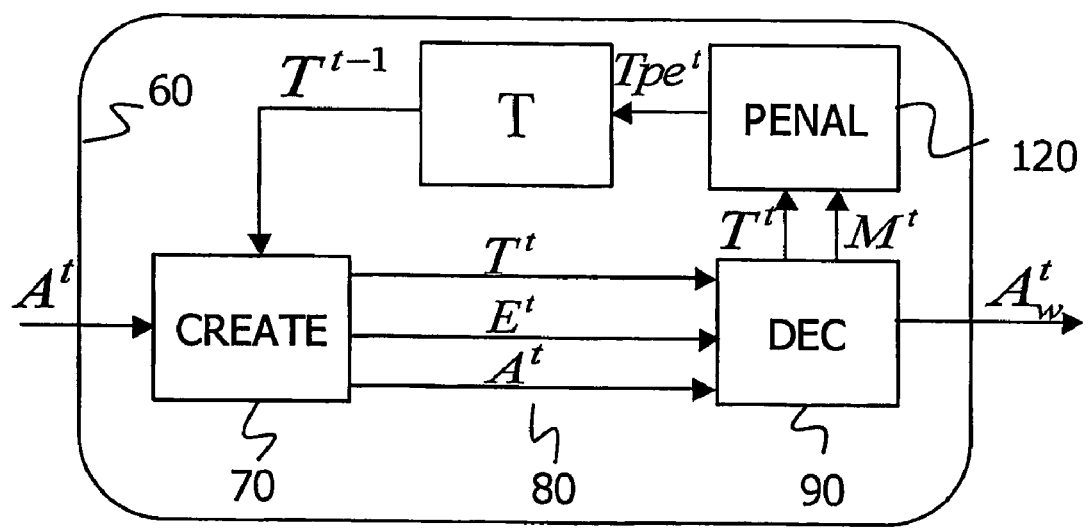
FIG. 9b is a functional block diagram of the temporal tracking means comprising contender penalizing means for penalizing losing tracks at time t, coming from the same track at time t−1 as a winning track at time t.

Due to the alarm-centric approach used in the preferred embodiment of the invention, a track at time t−1 $T_j^{t-1}$ may be divided into several "child" tracks at time t. Assuming that said track $T_j^{t-1}$ has a strong merit value, its "child" tracks will all inherit from said strong merit value $M_j^t$. Among them, however, only one can be chosen as a winning track $Tw_j^{t-1}$, as shown in FIG. 9a. Others are false or losing tracks, but are serious competitors of the winning track by virtue of their strong merit value, for building new tracks at time t+1 and beyond. In order to prevent said false tracks from having too much influence and inducing some errors in the track creation process, the temporal tracking means 30 further comprise contender penalizing sub-means 120 for penalizing said losing tracks at time t, coming from the same track at time t−1 as a winning track at time t. Said contender penalizing sub-means are shown in FIG. 9b. Said losing tracks at time t are transformed into penalized tracks $Tpe_j^t$ at time t. This transformation simply consists in applying a penalizing factor $f_p$ to the merit of any new track at time t+1, which associates a losing track with an alarm at time t+1. Said penalized merit criterion may be expressed as follows:

$MP_{i,j}^{t+1} = f_p \cdot [(1-\theta) \cdot \overline{E}_{i,j}^t + \theta \cdot \overline{S}_i^t]$, where $f_p$ is areal value greater than 1. Said value is strongly dependent on the application.

Figure 10:
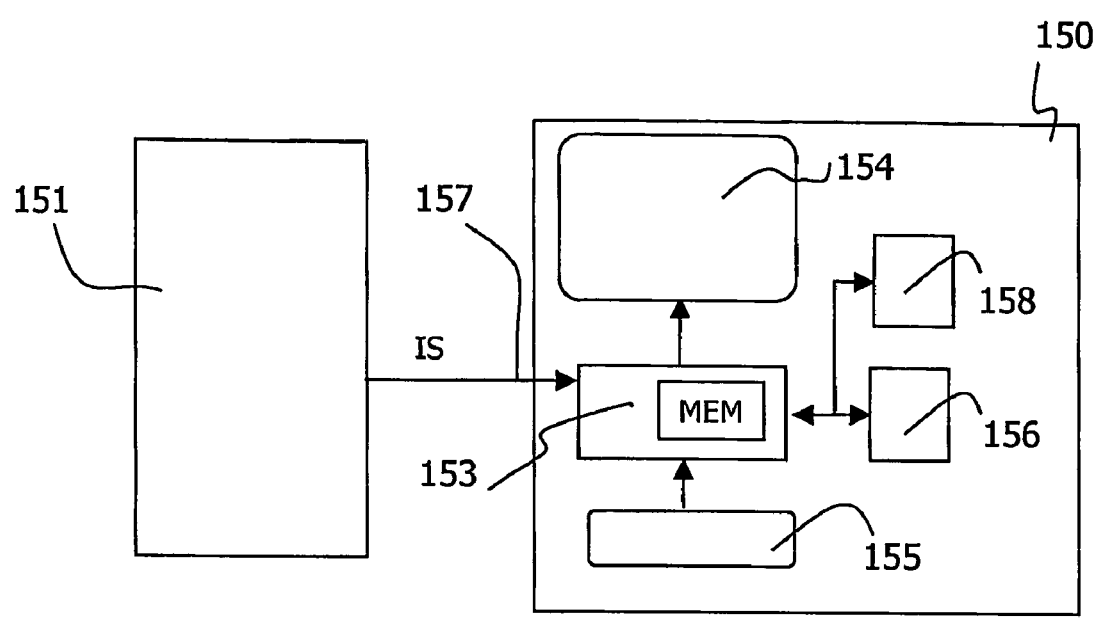
FIG. 10 is a functional block diagram of a medical examination apparatus using the system invention.

FIG. 10 shows the basic components of an embodiment of an image viewing system 150 in accordance to the present invention, incorporated in a medical examination apparatus. As indicated schematically in FIG. 10, said medical examination apparatus has acquisition means 151 for acquiring a sequence of images IS. Said sequence of images IS is processed by a processing device 153 comprising alarm detection means and temporal tracking means as described above.

The image viewing system 150 is generally used in the intervention room or near the intervention room for processing real time images. If steps of the present method are to be applied on stored medical images, for example for estimating medical parameters, the system for processing the data of the stored images will be called image viewing station. The medical examination apparatus provides the image data IS by connection 157 to the processing device 153. Said processing device 153 provides processed image data to display and/or storage means. The display means 154 may be a screen. The storage means may be a memory MEM of the processing system 153. Said storage means may be alternatively be external storage means. This processing device 153 may comprise a suitably programmed computer, or a special-purpose processor having circuit means such as LUTs, Memories, Filters, Logic Operators, that are arranged to perform the functions of the method steps according to the invention. The image viewing system 150 may also comprise a keyboard 155 and a mouse 156. Icons may be provided on the screen to be activated by mouse clicks, or special pushbuttons may be provided on the system to constitute control means 158 for the user to start, to control the duration of, or to stop the processing means of the system in chosen phases.

The present invention is applicable regardless of the medical imaging technology that is used to generate the initial data. Various modifications can be made to the order in which processing steps are performed in the above-described specific embodiment. The above-described processing steps applied to medical image data can advantageously be combined with various other known processing/visualization techniques.

The drawings and their description hereinbefore illustrate rather than limit the invention. It will be evident that there are numerous alternatives which fall within the scope of the appended claims. For instance, several objects of interest may be tracked. In this respect the following closing remarks are made: there are numerous ways of implementing functions by means of items of hardware or software, or both. In this respect, the drawings are very diagrammatic, each representing only one possible embodiment of the invention. Thus, although a drawing shows different functions as different blocks, this by no means excludes that a single item of hardware or software carries out several functions, nor does it exclude that a single function is carried out by an assembly of items of hardware or software, or both.

Any reference sign in a claim should not be construed as limiting the claim. Use of the verb "to comprise" and its conjugations does not exclude the presence of elements or steps other than those stated in a claim. Use of the article "a" or "an" preceding an element or step does not exclude the presence of a plurality of such elements or steps.

The invention claimed is:

1. A real time medical viewing system for enhancing an object of interest in a sequence of medical images, comprising:

alarm detection means (20) for detecting a set of alarms ($A^t$) of said object of interest in a medical image ($I^t$) at time t, temporal tracking means (30) comprising:

track creation sub-means (70) for iteratively creating a set of tracks ($T^t$) at time t by associating alarms of said set of alarms ($A^t$) with tracks ($T^{t-1}$) at time t−1, a track ($T_j^{t-1}$) at time t−1 comprising a predicted alarm ($Ap_j^t$) at time t and an association of an alarm ($A_i^t$) at time t with said predicted alarm ($Ap_j^t$) at time t forming a track ($T_j^t$) at time t, decision sub-means (80) for choosing a track ($T_j^t$) from among said set of tracks ($T^t$) at time t in accordance with a merit criterion ($M_{i,j}^t$), the alarm ($A_i^t$) of said track ($T_j^t$) at time t corresponding to a detection of said object of interest in said medical image at time t.

2. A real time medical viewing system as claimed in claim 1, wherein said track creation means (70) are able to associate, with an alarm ($A_i^t$) at time t, the track ($T_j^{t-1}$) at time t−1 that minimizes a matching error ($E_{i,j}^t$).

3. A real time medical viewing system as claimed in claim 2, wherein an alarm at time t is described by a vector of characteristics, and said matching error ($E_{i,j}^t$) is evaluated on the basis of distances between components of the vectors of characteristics (VC) of said alarm ($A_i^t$) at time t and said predicted alarm ($Ap_j^t$) of said track at time t−1.

4. A real time medical viewing system as claimed in claim 3, wherein said vector of characteristics (VC) of said alarm ($A_i^t$) comprises a barycenter position ($c_i^t$), a radius ($r_i^t$), and an angle ($\alpha_i^t$), and said matching error ($E_{i,j}^t$) comprises a barycenter error, a radius error, and an angle error.

5. A real time medical viewing system as claimed in claim 2, wherein said matching error ($E_{i,j}^t$) is a fuzzy error ($E_{Fzi,j}^t$).

6. A real time medical viewing system as claimed in claim 1, wherein an alarm ($A_i^t$) is given a strength measure ($s_i^t$), and said decision sub-means (80) are able to calculate said merit criterion ($M_{i,j}^t$), for an association of said alarm ($A_i^t$) with a track ($T_j^{t-1}$) at time t−1, as a combination of a temporally integrated alarm strength measure ($\overline{S}_i^t$) and a temporally integrated matching error ($\overline{E}_{i,j}^t$).

7. A real time medical viewing system as claimed in claim 1, wherein said temporal tracking means (30) comprise virtual track creation sub-means (110) for creating a virtual track ($TV_j^t$) at time t from an orphan track ($OT_j^t$) at time t−1 or from an orphan alarm at time t.

8. A real time medical viewing system as claimed in claim 1, wherein said temporal tracking means (30) comprise prediction sub-means (100) for predicting a track ($Tp_j^t$) at time t from a track ($T_j^t$) at time t−1.

9. A real time medical viewing system as claimed in claim 1, wherein said predicted alarm ($Ap_j^t$) at time t corresponds to the alarm ($A_i^{t-1}$) of said track at time t−1.

10. A real time medical viewing system as claimed in claim 1, wherein said temporal tracking means (30) comprise contender penalizing sub-means (120) for penalizing losing tracks at time t, that originate from the same track at time t−1 as a winning track ($Tw_j^t$) at time t.

11. An image processing method for use in a real-time medical viewing system capable of detecting an object of interest in a sequence of medical images and comprising:

a step (20) of detecting a set of alarms ($A^t$) of said objects of interests in a medical image ($I^t$) at time t, a step (30) of temporal tracking comprising the sub-steps of:

iteratively creating (70) a set of tracks ($T^t$) at time t by associating alarms of said set of alarms ($A^t$) with tracks ($T^{t-1}$) at time t−1, a track ($T_j^{t-1}$) at time t−1 comprising a predicted alarm ($Ap_j^t$) at time t and an association of an alarm ($A_i^t$) at time t with said predicted alarm ($Ap_j^t$) at time t forming a track ($T_j^t$) at time t, choosing (80) a track ($T_j^t$) from among said set of tracks at time t in accordance with a merit criterion ($M_{i,j}^t$), the alarm ($A_i^t$) of said track at time t corresponding to a detection of said object of interest in said medical image at time t.

12. A computer program product comprising a computer-readable medium having encoded thereon a set of instructions for carrying out on a computer an image processing method comprising:

detecting a set of alarms ($A^t$) of an object of interest in a medical image ($I^t$) at a time t;

iteratively creating a set of tracks ($T^t$) at time t by associating alarms of said set of alarms ($A^t$) with tracks ($T^{t-1}$) at a time t–1, each track ($T_j^{t-1}$) at time t–1 comprising a predicted alarm ($Ap_j^t$) at time t and an association of an alarm ($A_i^t$) at time t with said predicted alarm ($Ap_j^t$) at time t forming a track ($T_j^t$) at time t; and choosing a track ($T_j^t$) from among said set of tracks ($T^t$) at time t in accordance with a merit criterion ($M_{i,j}^t$) and penalizing losing tracks at time t, that originate from the same track at time t–1 as a winning track ($Tw_j^t$) at time t, the alarm ($A_i^t$) of said track ($T_j^t$) at time t corresponding to a detection of said object of interest in said medical image at time t.

13. A medical examination imaging apparatus comprising a viewing system as claimed in one of claims 1 to 9.

14. The method of claim 11, wherein said steps are carried out on a computer.

\* \* \* \* \*